(12) United States Patent
Cully et al.

(10) Patent No.: US 12,397,130 B2
(45) Date of Patent: Aug. 26, 2025

(54) INDWELLING LUMINAL DEVICES

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Matthew E. Maulding, Bellemont, AZ (US); Claudio Schonholz, Charleston, SC (US); Benjamin M. Trapp, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 270 days.

(21) Appl. No.: 18/104,507

(22) Filed: Feb. 1, 2023

(65) Prior Publication Data
US 2023/0173225 A1    Jun. 8, 2023

Related U.S. Application Data

(60) Division of application No. 16/853,441, filed on Apr. 20, 2020, now Pat. No. 11,571,544, which is a (Continued)

(51) Int. Cl.
*A61M 25/00* (2006.01)
*A61M 25/04* (2006.01)
(Continued)

(52) U.S. Cl.
CPC ...... *A61M 25/005* (2013.01); *A61M 25/0026* (2013.01); *A61M 25/0045* (2013.01); *A61M 25/0068* (2013.01); *A61M 25/0082* (2013.01); *A61M 25/04* (2013.01); *A61M 2025/0004* (2013.01); *A61M 25/0013* (2013.01); *A61M 2025/0019* (2013.01); *A61M 2025/0024* (2013.01); *A61M 2025/0031* (2013.01);
(Continued)

(58) Field of Classification Search
CPC .. A61M 2025/0004; A61M 2025/0034; A61M 2025/004; A61M 2025/0057; A61M 2025/0175; A61M 25/005
See application file for complete search history.

(56) References Cited

U.S. PATENT DOCUMENTS

| 3,173,418 A | 3/1965 | Baran |
|---|---|---|
| 4,451,252 A | 5/1984 | Martin |

(Continued)

FOREIGN PATENT DOCUMENTS

| CN | 1373679 A | 10/2002 |
|---|---|---|
| JP | 10-277147 A | 10/1998 |

(Continued)

OTHER PUBLICATIONS

International Preliminary Report on Patentability received for PCT Patent Application No. PCT/US2011/051062, mailed on Mar. 21, 2013, 7 pages.

(Continued)

*Primary Examiner* — Deanna K Hall

(57) ABSTRACT

The invention comprises an indwelling medical device which is capable of delivering a therapeutic agent evenly along the length of the indwelling portion, including the outer wall, of the device.

20 Claims, 14 Drawing Sheets

Related U.S. Application Data continuation of application No. 14/936,065, filed on Nov. 9, 2015, now Pat. No. 10,625,049, which is a continuation of application No. 13/228,330, filed on Sep. 8, 2011, now Pat. No. 9,180,274.

(60) Provisional application No. 61/381,358, filed on Sep. 9, 2010.

(51) Int. Cl.
*A61M 25/01* (2006.01)
*A61M 25/10* (2013.01)

(52) U.S. Cl.
CPC ............ *A61M 2025/0034* (2013.01); *A61M 2025/0036* (2013.01); *A61M 2025/004* (2013.01); *A61M 2025/0057* (2013.01); *A61M 2025/006* (2013.01); *A61M 2025/0073* (2013.01); *A61M 2025/0076* (2013.01); *A61M 2025/0175* (2013.01); *A61M 2025/1047* (2013.01); *A61M 2202/0283* (2013.01); *A61M 2202/04* (2013.01)

(56) References Cited

U.S. PATENT DOCUMENTS

| | | |
|---|---|---|
| 4,623,329 A | 11/1986 | Drobish et al. |
| 4,643,711 A | 2/1987 | Bates |
| 4,808,155 A | 2/1989 | Mahurkar |
| 5,049,132 A | 9/1991 | Shaffer et al. |
| 5,213,576 A * | 5/1993 | Abiuso ............ A61M 16/0456 604/101.02 |
| 5,269,755 A | 12/1993 | Bodicky |
| 5,476,453 A | 12/1995 | Mehta |
| 5,584,803 A | 12/1996 | Stevens et al. |
| 5,685,867 A | 11/1997 | Twardowski et al. |
| 5,695,457 A | 12/1997 | St. Goar et al. |
| 5,704,915 A | 1/1998 | Melsky et al. |
| 5,718,692 A | 2/1998 | Schon et al. |
| 5,775,327 A | 7/1998 | Randolph et al. |
| 5,820,607 A | 10/1998 | Tcholakian et al. |
| 5,947,953 A | 9/1999 | Ash et al. |
| 6,001,079 A | 12/1999 | Pourchez |
| 6,179,827 B1 | 1/2001 | Davis et al. |
| 6,190,349 B1 | 2/2001 | Ash et al. |
| 6,409,700 B1 | 6/2002 | Siegel et al. |
| 6,592,565 B2 | 7/2003 | Twardowski |
| 6,638,242 B2 | 10/2003 | Wilson et al. |
| 6,719,749 B1 | 4/2004 | Schweikert et al. |
| 6,758,836 B2 | 7/2004 | Zawacki |
| 6,872,198 B1 | 3/2005 | Wilson et al. |
| 6,881,211 B2 | 4/2005 | Schweikert et al. |
| 6,955,661 B1 | 10/2005 | Herweck et al. |
| RE39,451 E | 12/2006 | Kuhle |
| 7,569,029 B2 | 8/2009 | Clark |
| 7,635,358 B2 | 12/2009 | Tan |
| 7,837,692 B2 | 11/2010 | Mulholland et al. |
| 9,180,274 B2 | 11/2015 | Cully et al. |
| 11,571,544 B2 | 2/2023 | Cully et al. |
| 2001/0027309 A1 | 10/2001 | Elsberry |
| 2002/0052576 A1 | 5/2002 | Massengale |
| 2003/0216681 A1 | 11/2003 | Zhang et al. |
| 2004/0006305 A1 * | 1/2004 | Hebert ............ A61M 25/0021 604/509 |
| 2004/0097965 A1 | 5/2004 | Gardeski et al. |
| 2005/0228339 A1 | 10/2005 | Clark |
| 2006/0149192 A1 | 7/2006 | Deniega et al. |
| 2008/0015500 A1 | 1/2008 | Herweck et al. |
| 2009/0254064 A1 | 10/2009 | Boatman |
| 2010/0152698 A1 * | 6/2010 | Koehler ............ A61M 25/007 604/524 |
| 2016/0114123 A1 | 4/2016 | Cully et al. |
| 2020/0246583 A1 | 8/2020 | Cully et al. |

FOREIGN PATENT DOCUMENTS

| | | |
|---|---|---|
| JP | 2002-519095 A | 7/2002 |
| JP | 2006-528906 A | 12/2006 |
| JP | 2007-330688 A | 12/2007 |
| WO | 01/05210 A2 | 1/2001 |
| WO | 2008/024714 A1 | 2/2008 |
| WO | 2009/002855 A2 | 12/2008 |
| WO | 2010/033698 A1 | 3/2010 |
| WO | 2012/034056 A1 | 3/2012 |

OTHER PUBLICATIONS

Search Report and Written Opinion of PCT/US2011/051062, mailed Sep. 9, 2010, 9 pages.

* cited by examiner

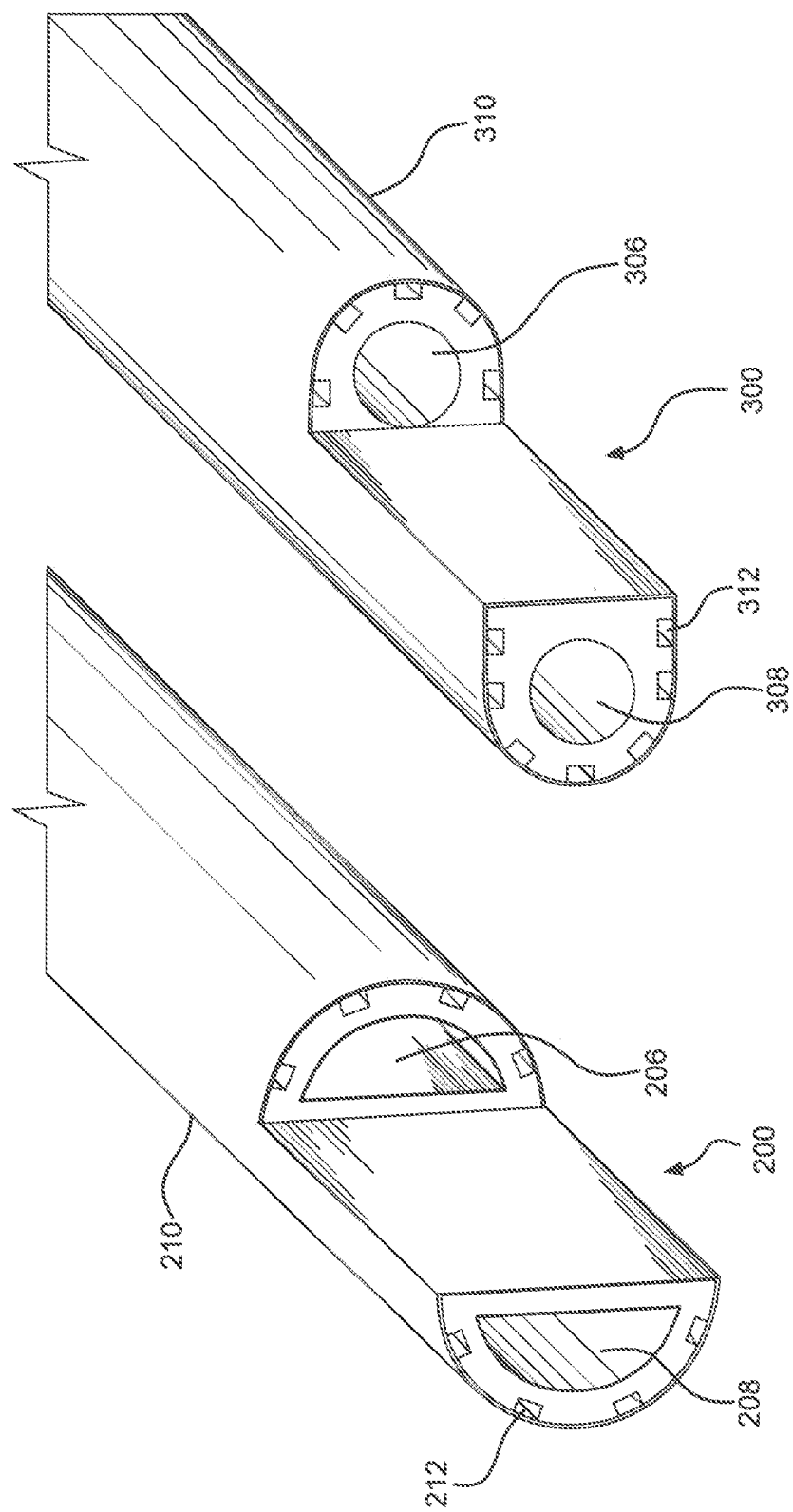

INDWELLING LUMINAL DEVICES

CROSS-REFERENCE TO RELATED APPLICATION

This application is a continuation of U.S. patent application Ser. No. 16/853,441, filed on Apr. 20, 2020, now U.S. Pat. No. 11,571,544, issued Feb. 7, 2023, which is a continuation of U.S. patent application Ser. No. 14/936,065, filed Nov. 9, 2015, now U.S. Pat. No. 10,625,049, issued Apr. 21, 2020, which is a continuation of U.S. patent application Ser. No. 13/228,330, filed Sep. 8, 2011, now U.S. Pat. No. 9,180,274, issued Nov. 10, 2015, which claims priority to U.S. Provisional Patent Application No. 61/381,358, filed Sep. 9, 2010, which are hereby incorporated by reference herein in their entireties.

FIELD OF INVENTION

The invention relates generally to medical devices for the treatment of various medical conditions and specifically to indwelling catheters used to treat a patient's bloodstream.

BACKGROUND OF THE INVENTION

Implanted medical devices such as venous and arterial catheters, neurological prostheses, wound drains, urinary catheters, central venous catheters, peritoneal catheters, shunts, and other luminal indwelling devices, are useful for treating various medical conditions. However, a drawback of implanted medical devices is the risk of infection while the medical device is inserted in the body, and thereafter. Such risk exists even though the medical devices are sterilized and carefully packaged to guard against introduction of microbes or pathogens during implantation or insertion of the medical device. For example, there is a risk of serious nosocomial infections when using catheters for hemodialysis procedures. In fact, central venous catheters account for most nosocomial catheter-related bloodstream infections.

When catheters and other indwelling luminal devices are inserted into body cavities such as the urinary tract, venous or arterial vessels, bacteria or other microbes can be picked up from the skin and carried into the insertion site where bacterial or microbial colonization may ensue. Infections may derive from an interaction of the microbes and the catheter micro-surface. Once infected, the microorganisms adhere to the catheter micro-surface and rapidly become encased in a polysaccharide matrix or biofilm, which protects the microorganisms from a host's defenses.

In the case of urinary and venous catheters, there is a significant threat of microbial growth along the exterior surface or outer wall of the catheter and, especially for catheters used long-term, there is a significant threat of microbial growth along the interior surface or inner wall. This can lead to chronic urinary tract infections (CUTI), or septicemia in the case of venous and arterial catheters, thrombolytic emboli, stenosis, and thrombosis resulting from infections, and other life threatening complications, especially among the elderly and immuno-compromised patients. Thus, there is a need for the development of better methods of preventing and treating infections caused by the insertion of catheters into a patient's body.

In addition to antimicrobials, other therapeutic agents may help reduce complications associated with chronically implanted indwelling medical devices in the body of a patient. Such medications include anti-inflammatoirenti-proliferatives and anti-coagulating agents or a combination thereof. However, to be effective the therapeutic agent should be delivered to a substantial portion of the surface of the indwelling medical device. Without such therapeutic agents, there is a risk that portions of the medical device will become compromised and cause an inflammatory response and/or allow tissue in-growth over surfaces of the indwelling portion of the medical device.

Other drawbacks of conventional indwelling catheters include a significant crossing profile, lack of convenience, and tissue damage to the areas to which the catheters are deployed. For example, indwelling catheters are typically used only periodically. As a result, inconvenient characteristics of catheters, such as being difficult to thread or insert catheter bodies, add to the treatment time and potential discomfort of therapy provided by the catheter. Also, as discussed above, indwelling catheters, such as central venous catheters, may cause damage to a patient's vasculature.

Accordingly, there is a need for a medical device that can effectively deliver a therapeutic agent to a substantial portion of its surface, e.g. a substantial length of the outer surface of an indwelling catheter. In addition, improved devices are needed which feature a lower profile, more convenient method of use, and reduce tissue damage caused to a patient's anatomy.

SUMMARY OF THE INVENTION

One embodiment of the invention comprises an indwelling catheter having a central tube with at least one lumen and an outer jacket surrounding said tube. In various embodiments, the indwelling catheter is a central venous catheter. In various embodiments, the catheter further comprises a plurality of grooves in the outer surface of the central tube, wherein the grooves and jacket form a plurality of channels extending along at least a portion of the longitudinal axis of the catheter.

In one embodiment, the central tube is internally segmented into a plurality of lumens. In another embodiment, the central tube comprises two lumens. In another embodiment, the outer surface of the central tube is generally circular. In another embodiment, the outer surface of the central tube is generally an oval. In another embodiment, the cross-section of the lumen is d-shaped. In another embodiment, the cross-section of the lumen is circular.

In various embodiments, said lumens are each in fluid communication with at least one extension tube. In another embodiment, the extension tubes each comprise a connector hub. In another embodiment, the channels are in fluid communication with an extension tube. In another embodiment, at least two extension tubes are in fluid communication with different channels. In another embodiment, the channels are in deflectable legs which can be positioned against the walls.

In various embodiments, the jacket is permeable. In various embodiments, the jacket is porous. In another embodiment, the jacket comprises ePTFE.

In various embodiments, the catheter further comprises a secondary tube. In various embodiments, the secondary tube concentrically surrounds the central tube and jacket. In other embodiments, the secondary tube spirals around the surface of the central tube and jacket. The secondary tube may also comprise a sleeve inserted into the patient's vasculature.

DESCRIPTION OF THE DRAWINGS

FIGS. 3A and 3B illustrate the distal end of the indwelling catheters depicted in FIGS. 2A and 2B.

DETAILED DESCRIPTION OF THE INVENTION

Figure 1:
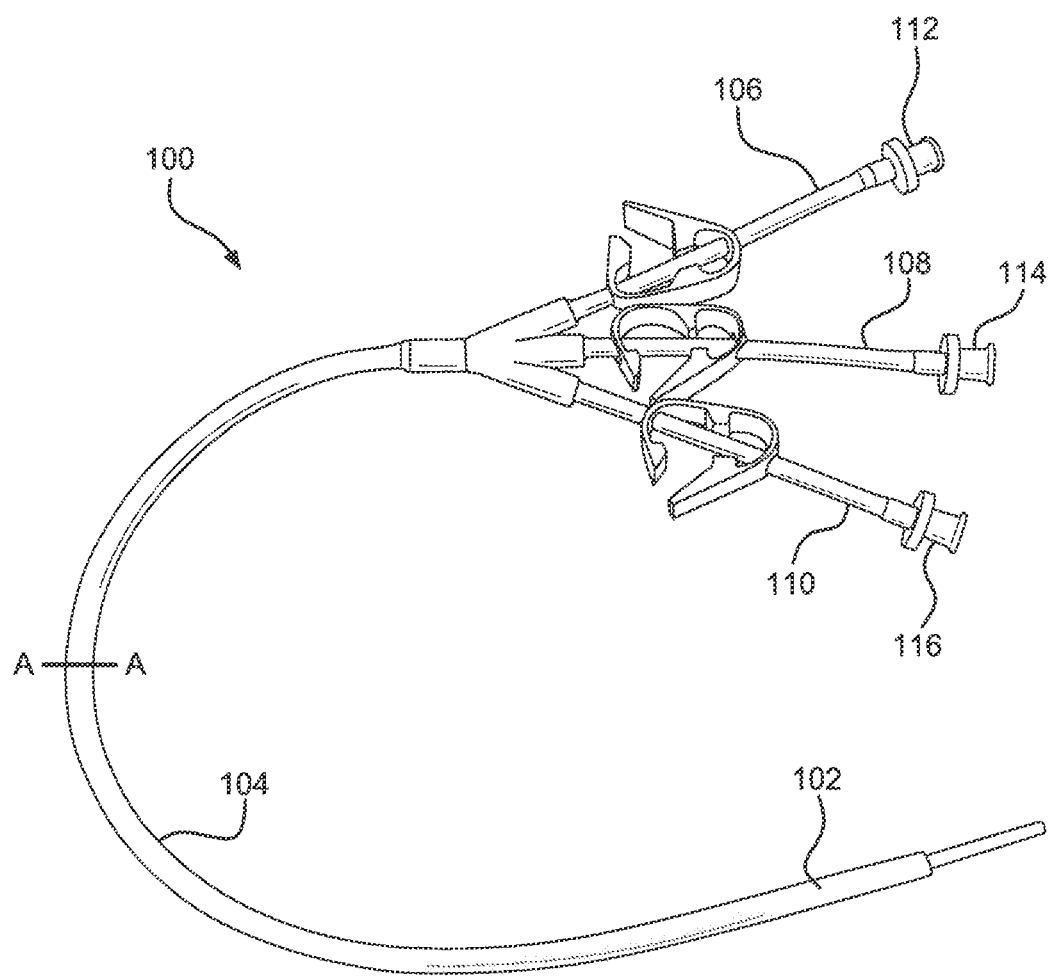
FIG. 1 illustrates an exemplary medical device which comprises an indwelling catheter and extension tubes.

While the present invention will hereinafter be described in connection with the preferred embodiments, it will be understood that it is not intended to limit the invention to these embodiments. Instead, it is intended to cover all alternatives, modifications, and equivalents as may be included within the spirit and scope of the invention as described and claimed.

For the purposes of the following description and the claims appended hereto, the term "distal" refers to those portions of a medical device, such an indwelling catheter, and those portions of components of the medical device which are nearest the insertion tip, that is, the end of the medical device that is inserted into an area of a patient's body, such as a blood vessel. Conversely, the relative term "proximal" refers to those portions of a medical device and those portions of components which are farthest from the insertion tip of the catheter.

Various exemplary medical devices in accordance with the disclosure comprise a central tube with at least one lumen, a second lumen, and an outer jacket concentrically surrounding the central tube. In various exemplary embodiments, the second lumen is comprised within the central tube and the two lumens are of equal cross-sectional surface area. In other exemplary embodiments, the second lumen is configured annularly between the outer surface of the central tube and the inner surface of the outer jacket. In yet other exemplary embodiments, the medical device comprises a secondary tube which comprises the second lumen.

In another embodiment of the invention, the medical device comprises an indwelling catheter. Said indwelling catheter can comprise a portion that is accessible from outside the body once said indwelling portion is inserted into the body. Any catheter used for medical treatment can generally be used for the present invention. Suitable catheters include, but are not limited to, venous, arterial, urinary catheters, wound drains, central venous catheters, peritoneal catheter, percutaneous catheters, sheaths and trocars, drainage catheters, endoscopes and endoscopic catheters, and gastrointestinal catheters. In addition to catheters, other medical devices that are insertable into the body of a patient, and accessible through the skin or other method once implanted can be used in the present invention. For example, the following other indwelling medical devices may be used: cannulas, cardiac pacing leads or lead tips, cardiac defibrillator leads or lead tips, implantable vascular access ports, blood tubing, vascular or other grafts, intra-aortic balloon pumps, heart valves, cardiovascular sutures, total artificial hearts and ventricular assist pumps.

Referring to the drawings, like reference numbers represent like or corresponding elements in the drawings. The drawings illustrate one embodiment of the instant invention. Other medical devices are also contemplated as part of the instant invention.

With reference to FIG. 1, exemplary medical device 100 is illustrated. Medical device 100 comprises an indwelling catheter 104. Medical device 100 further comprises extension tubes 106, 108 and 110, which are in fluid communication with lumens and channels (or annual spaces) within indwelling catheter 104. Medical device 100 further comprises connector hubs 112, 114 and 116, which are attached to the proximal ends of extension tubes 106, 108 and 110, respectively.

The proximal portion of medical device 100 comprises a central tube 102 which houses a plurality of single lumen proximal extension tubes, 106, 108 and 110. Proximal extension tubes 106, 108, and 110 each have a distal end and a proximal end. The distal end of each proximal extension tube is connected to the proximal end of central tube 102 such that the single lumen of each proximal extension tube is in fluid communication with one of the plurality of lumens of central tube 102. In addition, at least one single lumen extension tube is attached to a plurality of channels (not shown). In another embodiment, several extension tubes can be attached to the plurality of channels. In another embodiment, extension tubes 106, 108 and 110 may be removable.

In one embodiment, medical device 100 comprises a polymer, such as polyethylene, polyurethane, polycarbonates, ethyl vinyl acetate, polyamides (such as PEBAX®, a registered trademark of Arkema), polyimides, or similar material.

Figure 2A:
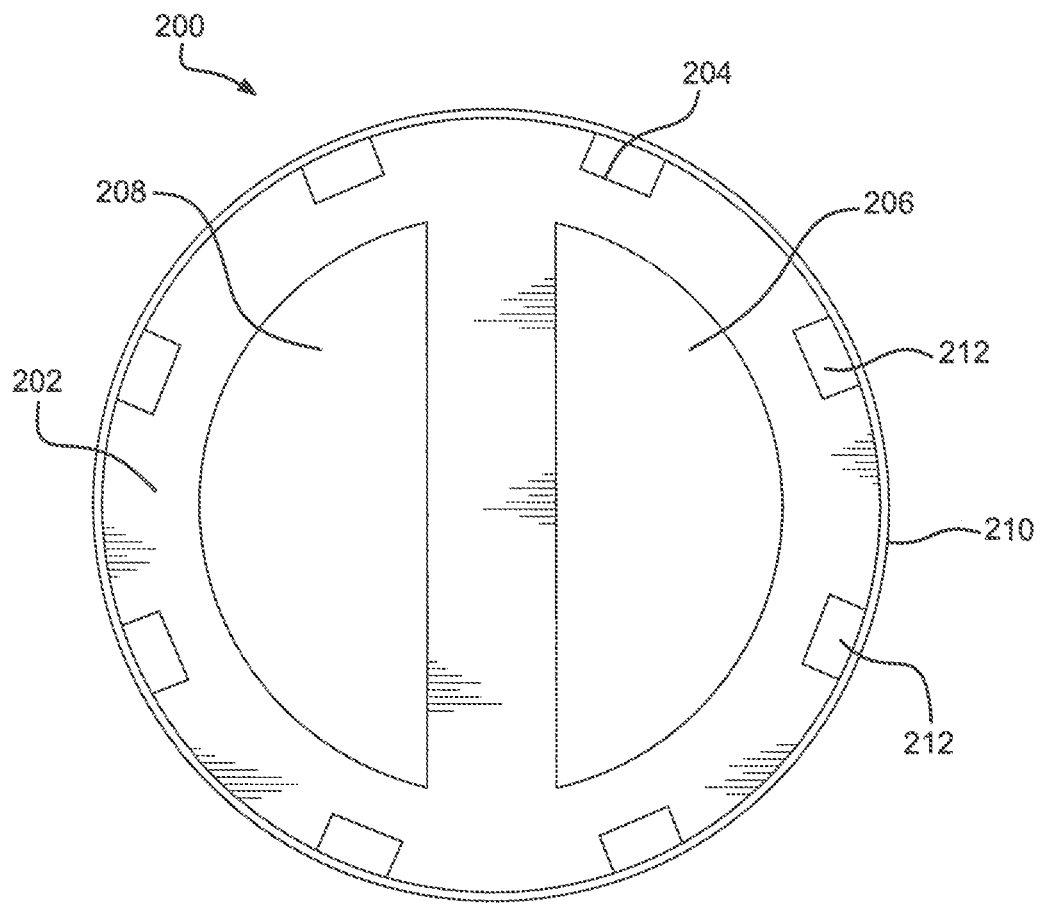
FIGS. 2A and 2B illustrate cross sections of two exemplary indwelling catheters at "A-A" in FIG. 1.

FIG. 2A illustrates a cross-sectional view of an exemplary medical device 200 at "A-A" in FIG. 1. Central tube 202 of medical device 200 is generally circular. Central tube 202 comprises a biocompatible polymeric material. A biocompatible material is hereby defined as a material being suited for and meeting the purpose and requirements of a medical device, used for either long or short term implants or for non-implantable applications. Long term implants are defined as items implanted for more than 30 days. Exemplary polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyether-amides, polyesters, polyimides, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins, and other various copolymers.

In an aspect of exemplary medical device 200, central tube 202 is internally segmented into lumens 206 and 208. Lumens 206 and 208 are parallel and have substantially the same "d-shaped" cross-sectional surface area.

In various exemplary embodiments, central tube 202 and jacket 210 comprise a highly flexible material, such as ePTFE. In this configuration, central tube 202 and jacket 210 are sufficiently flexible such that they are buoyant in the blood flow within the vessel. The flexible material also provides adequate support to allow medical device 200 to retain its overall shape while in operation. For example, central tube 202 has sufficient column strength to prevent the tube from collapsing when vacuum or suction is applied to it during a medical procedure. This flexibility and buoyancy helps to reduce the force and/or impact at which that medical device 200 makes contact with the walls of the treatment vessel, thereby minimizing tissue damage and reducing the likelihood of occurrences of vascular stenosis.

In various exemplary embodiments, central tube 202 further comprises heparin. Heparin may be attached to any surface of the central tube 202. A coating of heparin can help prevent and/or reduce thrombosis formation on or in central tube 202. In one exemplary embodiment, the surfaces of lumens 206 and 208 comprise a heparin coating. In another embodiment, the outer surface of central tube 202 comprises a heparin coating. The heparin coating and method of attaching a heparin coating is taught in U.S. Pat. No. 6,559,132, which is incorporated by reference herein in its entirety for all purposes.

One embodiment of the invention comprises an indwelling medical device that can effectively deliver a therapeutic agent evenly along the length, of said medical device. For the purposes of this invention "length" comprises at least a portion of the length of a medical device and its surface (i.e. outer wall), unless otherwise stated.

In this regard, in exemplary embodiments, central tube 202 further comprises a plurality of grooves 204 extending along its longitudinal axis. Grooves 204 may be positioned in the outer surface of central tube 202. In this configuration, the combination of grooves 204 and outer jacket 210 forms a plurality of channels 212 extending along the longitudinal axis of said central tube and jacket. In one aspect of the exemplary embodiment, grooves 204 are formed during extrusion of central tube 202. In another aspect, grooves 204 are formed by cutting the grooves into the outer wall of central tube 202, such as, for example, with a laser. Further, grooves 204 may be formed by reflowing the outer surface of central tube 202 around longitudinal features.

One of the advantages of having channels 212 along the longitudinal axis of the medical device is that when a fluid is infused into the channels, it evenly distributes the fluid along its length which can then diffuse to the outer wall of the medical device and/or to the surrounding environment in which the medical device is dwelling.

Grooves 204 may be configured in any shape, e.g. square, round or combinations thereof. Grooves 204 may continue down the entire length of central tube 202 or a portion thereof. In various exemplary embodiments, channels 212, which are formed by grooves 204 interfacing with jacket 210, carry liquids and/or gases from the proximal end to the distal end of medical device 202.

Jacket 210 of medical device 200 may comprise a permeable and/or porous material. Examples of such porous materials include, but are not limited to, porous fluoropolymers such as expanded polytetrafluoroethylene (ePTFE), expanded high density polyethylene (HDPE). Other non-porous polymers such as polyesters, polyurethanes, polyethylenes, polyimides, etc. can also be of utility provided they are processed to have pores. Examples of such processes include laser perforation and pin perforations. Jacket 210 may also comprise semi-permeable films, such as polyurethanes, silicones, and polyether-amides. As used herein, the term "porous" describes a material that contains small or microscopic openings, or pores. Without limitation, "porous" is inclusive of materials that possess pores that are observable under microscopic examination. The term "porous" describes a material through which fluids (liquid and/or gas) can penetrate through bulk flow. A permeable material prevents bulk flow while allowing selective molecules to pass, while a porous material can allow bulk flow while restricting flow of certain size particles.

Selecting porosity and/or permeability of the jacket material can generate a back pressure within channels 212 which aids in an even distribution of fluid down the length of the device, as opposed to a more porous or permeable structures that provide for flow to only a section of channels 212 with the least resistance. For example, if medical device 200 is located against the wall of a vessel, flow may be restricted and therapeutic agents will only be delivered to the sections that are not in contact with the vessel. If there was a jacket 210 that comprises a material with sufficient back pressure, the effect of wall contact on distribution will be minimized. Such a material can be designed, inter alia, by adjusting the porosity and/or permeability of the jacket material. Furthermore said jacket material may be adjusted by taking into account (or adjusting) the physical properties of the fluid (including any active agents and/or excipients in the fluid) by methods known in the art.

A therapeutic agent is a drug or agent that can elicit a bioactive response. Examples of the therapeutic agents or drugs useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, atorvastatin, simvastatin, pravastatin, fluvastatin, lovastatin, cephalexin, erythromycin, haloperidol, zomepirac, ferrous lactate, vincamine, phenoxybenzamine, diltiazem, milrinone, captopril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylinend imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor. In an exemplary embodiment, the therapeutic agent is a steroid, such as dexamethasone. Additional exemplary embodiments comprise therapeutic agents consisting of mixtures of anti-microbials, antivirals, antibiotics, antibacterial agents, anti-inflammatory agents, anti-proliferative agents, anti-coagulating agents, hemostatic agents, decongestants, hemorrhoidal treatments, and/or analgesics.

The fluid interaction with jacket 210 is important for even distribution. If the therapeutic agent to be delivered to the vasculature is of high viscosity or has a surface energy that restricts and/or prevents passage through jacket 210, the pore size, structure and/or surface energy of jacket 210 can be tailored to obtain the optimized fluid mechanics for a desired dosing regimen. In an exemplary embodiment, a therapeutic agent is substantially evenly distributed along the length of the medical device. In an aspect of these embodiments, jacket 210 is a highly porous material, which allows a substantial amount of therapeutic agent to evenly perfuse out along the length of medical device 200. In other aspects of these embodiments, jacket 210 has a low degree of porosity, and therefore the therapeutic agent may dwell within the channel 212 and wick out slowly over a period of time.

For example, if wicking of the therapeutic agent is used to either provide for a slow delivery (spanning the course of multiple hours, days and/or treatment cycles) or a more even delivery of a therapeutic agent, then the microstructure and surface energy of jacket 210 must be tailored to allow for wicking of the therapeutic agent. Wicking may be used to provide a therapeutic agent to the areas of outer jacket 210 that are over the non-grooved portions of the surface of central tube 202.

In addition, channels 212 may be designed to function as a reservoir to allow for the storage of an appropriate amount of a therapeutic agent. For instance, if the device is intended to supply a therapeutic agent to the surface of jacket 210 over the course of multiple days, and the rate of delivery is known, the required volume for channels 212 to function as reservoirs can be calculated. If additional volume is required, an additional reservoir can be located external to the patient or in an additional volume internal to the central tube 202.

In various exemplary embodiments, jacket 210 further comprises a heparin coating. In various embodiments, both jacket 210 and the outer surface of central tube 202 comprise a heparin coating.

In various exemplary embodiments, jacket 210 may further comprise a coating of therapeutic agents. In some exemplary embodiments, the therapeutic agent would be bound to the outer surface of jacket 210. In other embodiments, the therapeutic agent would pass through jacket 210 into the vasculature via pores or permeations in jacket 210.

In other exemplary embodiments, jacket 210 comprises a hydrogel coating. In these configurations, therapeutic agents may be absorbed by the hydrogel as they exit the pores and/or permeations in jacket 210. The therapeutic agents may also be formed as a hydrogel and applied to the surface of or otherwise dissociating from jacket 210. The therapeutic agent would be released by the hydrogel into the blood stream at a significantly slower rate, preventing the drug from sloughing off of jacket 210. In yet other exemplary embodiments, a beneficial gas, such as nitrous oxide, may be passed through channels 212 and out of jacket 210 into the patient's blood stream.

Figure 2B:
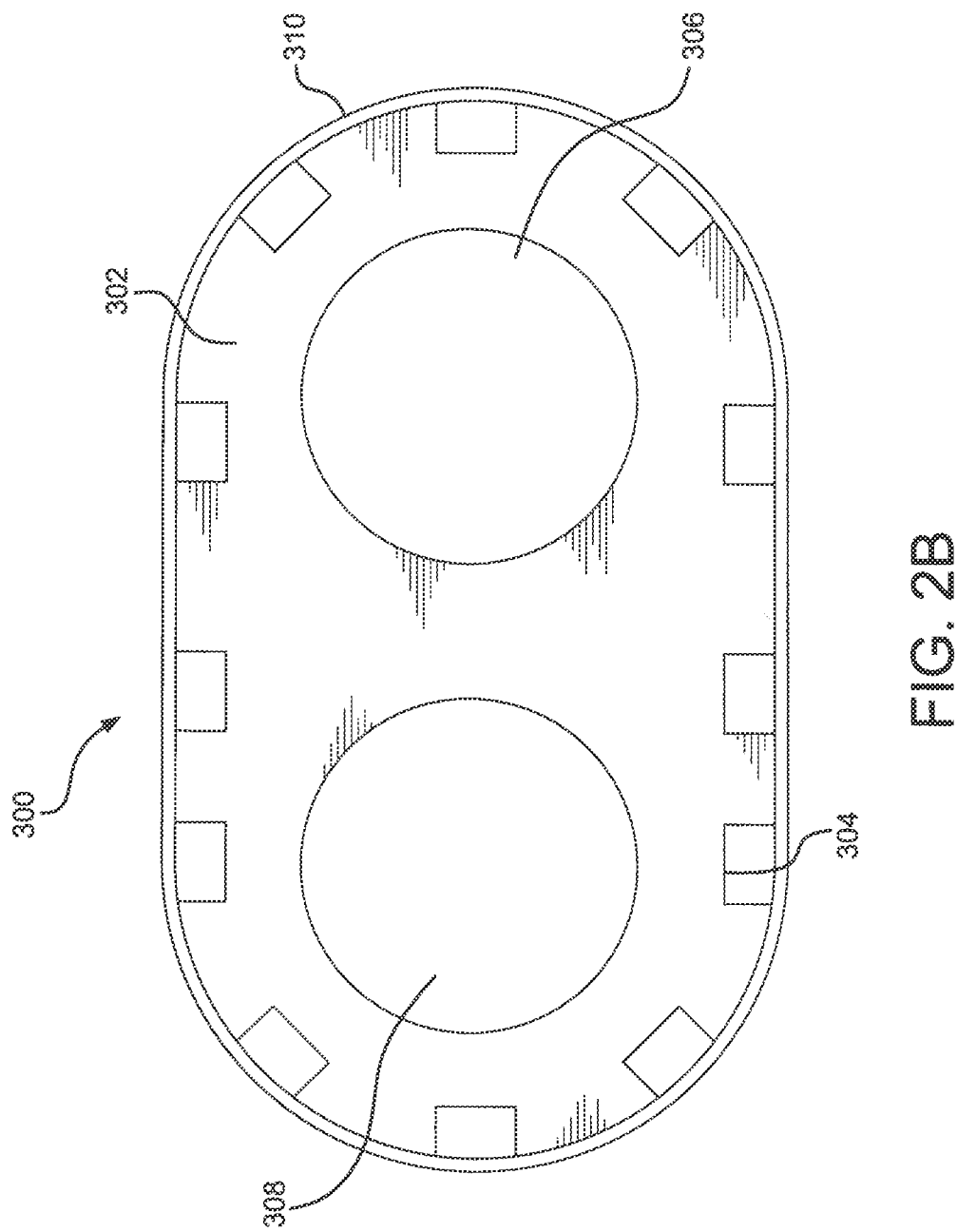

With reference to FIG. 2B an exemplary medical device 300 is illustrated. Medical device 300 comprises a central tube 302, grooves 304, and an outer jacket 310. In this exemplary embodiment, central tube 302 is generally oval in shape, and is segmented into lumens 306 and 308. Lumens 306 and 308 are substantially parallel and have the same general circular shape. In an aspect of the exemplary embodiment, lumens 306 and 308 may have substantially the same cross-sectional surface area.

FIGS. 3A and B illustrate the distal end of the exemplary medical devices depicted in FIGS. 2A and 2B. Specifically, FIG. 3A illustrates the distal end of medical device 200. FIG. 3B illustrates the distal end of medical device 300. As illustrated in FIGS. 3A and 3B, the lumens 206, 208, 306 and 308 extend from the proximal to the distal end of the medical device. However, in a preferred embodiment, the channels will not be open at the distal end so that when fluid is infused into the channel, the fluid will not flow out of the distal end of the channel.

Figure 4A:
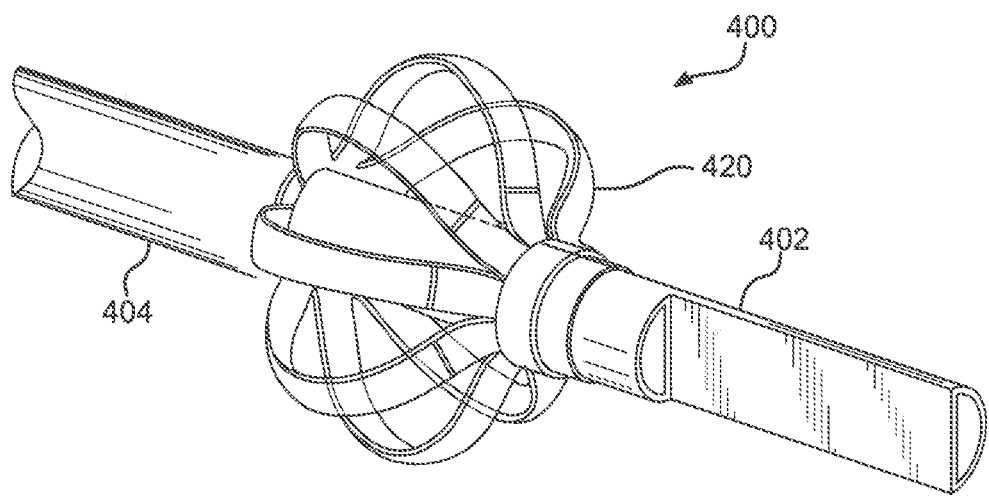
FIGS. 4A and 4B illustrate, respectively, a perspective view and a cross section of an exemplary medical device comprising a "Chinese lantern" type anchoring device.
Figure 4B:
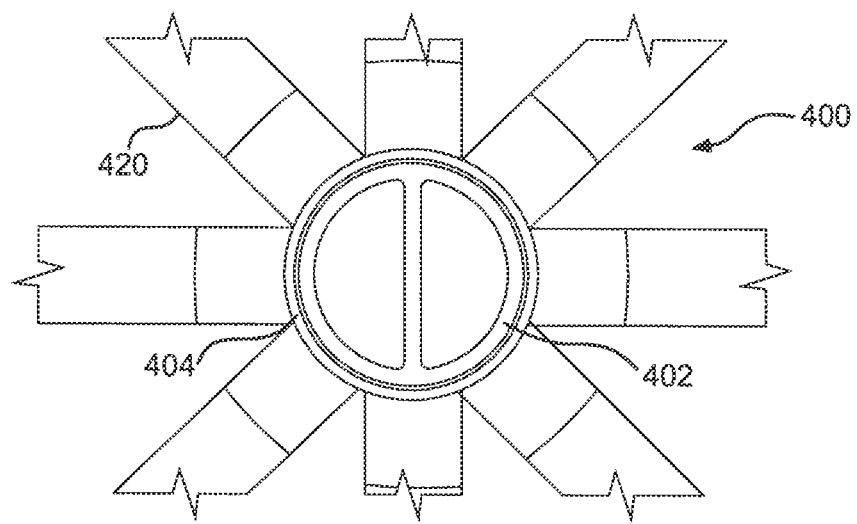

With reference to FIGS. 4A and 4B, an exemplary medical device 400 is illustrated. Medical device 400 further comprises an anchor segment 420 of outer tube 404. Anchor segment 420 may be located at the distal end of outer tube 404. In an aspect of the exemplary embodiment, anchor segment 420 may comprise a series of "legs" which are in contact with the vessel walls, and act to center and stabilize medical device 400 within the vessel. Such a configuration may help to minimize the risk of venous stenosis by preventing medical device 400 from damaging and/or abrading adjacent tissues.

In an aspect of the exemplary embodiment, the anchor segment 420 may be configured as a "Chinese lantern" shape. In this configuration, the legs of anchor segment 420 may be deployed from a relaxed configuration, in which they are substantially parallel to central tube 402, to an expanded configuration, in which they contact the vessel walls in a "Chinese lantern" shape. In a preferred embodiment, central tube 402 is fixedly attached to the distal end of anchoring segment 420. Central tube 402 is partially withdrawn axially through outer tube 404, which causes the legs of anchoring segment 420 to expand and contact the walls of the treatment vessel.

Anchor segment 420 may further comprise at least one individual lumen within each "leg" with communication to the outside surface via holes or ports. In this configuration, therapeutic agent may be delivered through the individual lumens directly to the point where the legs of anchor segment 420 contact the vessel wall. In another aspect of the exemplary embodiment, the legs of anchor segment 420 are configured as a tubular construct having a plurality of grooves on their outer periphery. The grooves may deliver therapeutic agents directly to the vessel walls. Outer tube 404 may comprise a material of sufficient porosity and/or permeability to deliver therapeutic agents at the points which outer tube 404 contacts the vessel wall, thereby efficiently delivering smaller doses of therapeutic agents directly to targeted tissue and preventing drugs from washing downstream into the circulatory system.

Figure 5:
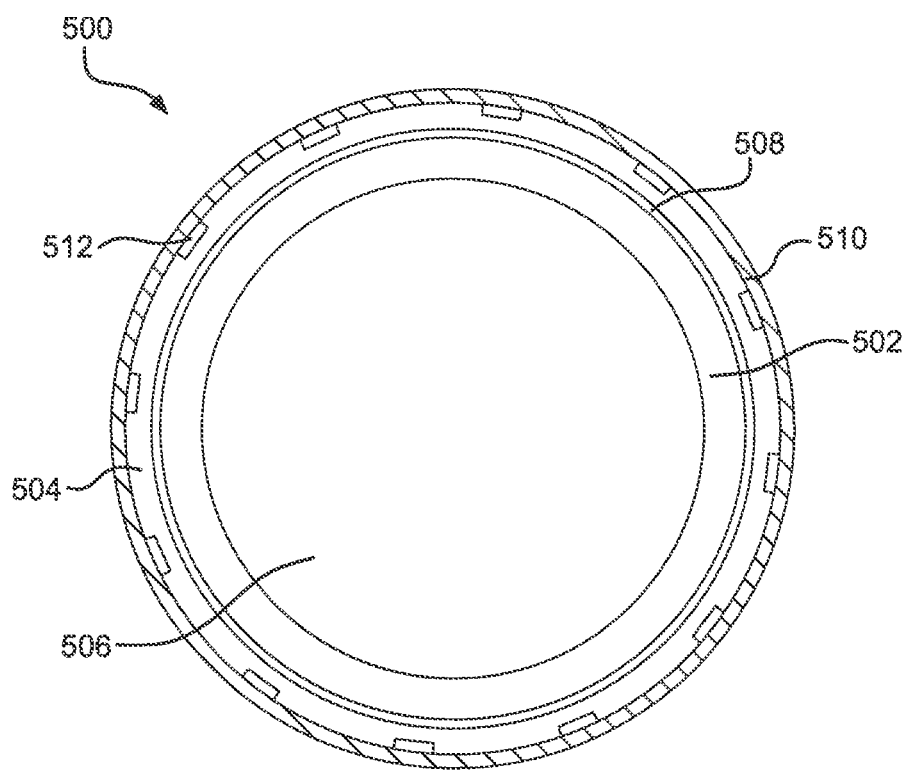
FIG. 5 illustrates a cross section of an exemplary medical device.

With initial reference to FIG. 5, in various exemplary embodiments, medical device 500 comprises a central tube 502, an outer tube 504 and an outer jacket 510. Outer tube 504 concentrically surrounds central tube 502, creating an annular lumen 508. Outer jacket 510 concentrically surrounds the outer surface of outer tube 504. Central tube further comprises a central lumen 506.

In various exemplary embodiments, outer tube 504 further comprises a plurality of grooves 512 extending along its longitudinal axis. Grooves 512 may be positioned in the outer surface of outer tube 504. In this configuration, a plurality of channels extend along the longitudinal axis of outer tube 504 and outer jacket 510. As discussed earlier in relation to exemplary medical device 200, grooves 512 may be formed, for example, by cutting grooves into the outer wall of outer tube 504, reflowing the outer surface of outer tube 504, or created during extrusion of outer tube 504.

In various exemplary embodiments, these channels may be in fluid communication with a supply of beneficial drugs or agents. As previously discussed in relation to exemplary medical device 200, the microstructure of jacket 510 and position and configuration of the channels may control the flow rate of a beneficial drug or agent into the treatment vessel.

Figure 6A:
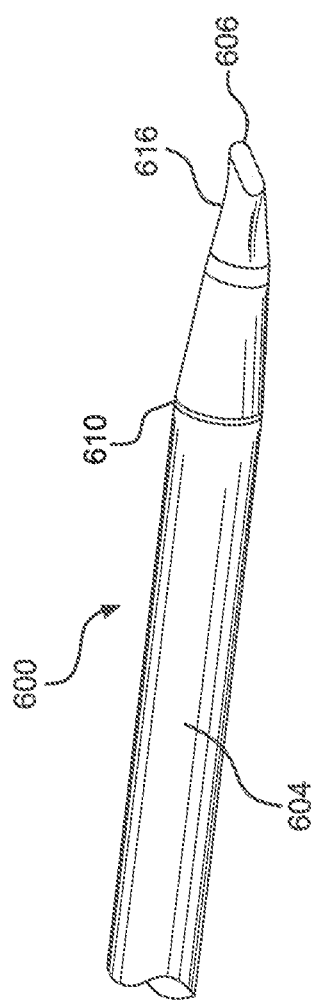
FIGS. 6A and 6B illustrate side views of an exemplary medical device.
Figure 6B:
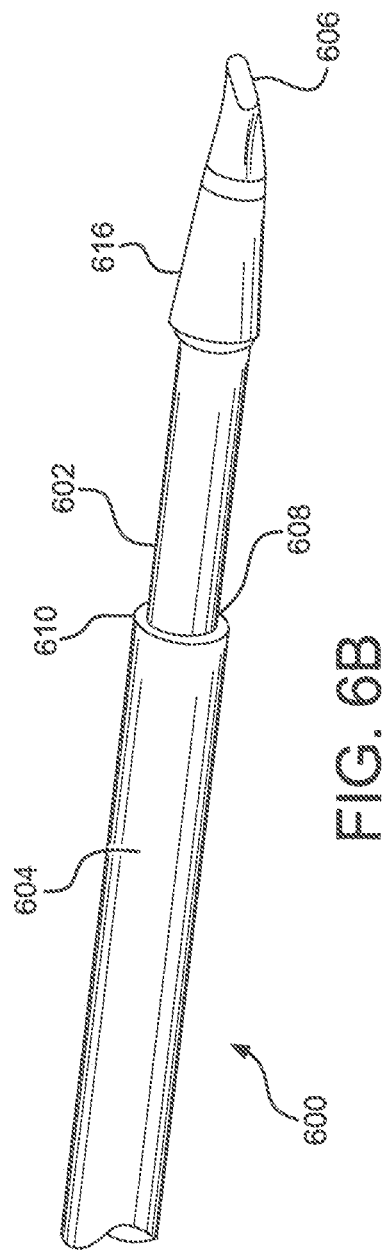

With reference to FIGS. 6A and 6B, in various exemplary embodiments, medical device 600 comprises a central tube 602, an outer tube 604, and a jacket 610. Outer tube 604 concentrically surrounds central tube 602, creating an annular lumen 608. Jacket 610 concentrically surrounds outer tube 604. In accordance with an aspect of the exemplary embodiment, central tube 602 may be longer than outer tube 604 and jacket 610, therefore protruding from outer tube 604 and jacket 610 at their distal ends.

In various exemplary embodiments, outer tube 604 further comprises a plurality of grooves extending along its longitudinal axis. These grooves may be positioned in the outer surface of outer tube 604. In this configuration, a plurality of channels extending along the longitudinal axis of outer tube 604 and outer jacket 610. These channels may be in fluid communication with a supply of beneficial drugs or agents. As previously discussed in relation to exemplary medical device 200, the microstructure of jacket 610 and position and configuration of channels may control the flow rate of a beneficial drug or agent into the treatment vessel.

In various exemplary embodiments, medical device 600 may further comprise a distal tip 616 attached to the distal end of central tube 602. Distal tip 616 may comprise opening 606 and terminate in a tip. In various exemplary embodiments, distal tip 616 is wedge, "duck-bill," or flapper-shaped. However, any shape of distal tip 616 which allows for treated blood to exit through opening 606 is within the scope of the present disclosure.

In this configuration, the distal tip 616 protrudes from the outer tube 604 when medical device 600 is in operation, as illustrated in FIG. 6B. During operation, blood to be treated flows in to medical device 600 through annular lumen 608. The blood is treated outside of the body, and the treated blood flows back in to the vessel through opening 606 and as the blood exits distal tip 616. When medical device 600 is not in operation, as illustrated in FIG. 6A, distal tip 616 may be retracted such that it seats inside the distal end of outer tube 604, sealing the end of annular lumen 608. Any shape and configuration of distal tip 616 which provides a return path for treated blood and is capable of sealing lumen 608 when the medical device is not in operation is within the scope of the present disclosure. In addition, any shape of lumen, including annular or one or more channels, which provides an outflow path for blood from the vessel is within the scope of the present invention.

In various exemplary embodiments, distal tip 616 comprises a relatively soft biocompatible material, such a silicone. In such embodiments, central tube 602 may comprise a more rigid biocompatible material, such as polyurethane. A more rigid material than is used in other exemplary embodiments is permissible in this configuration because central tube 602 is only exposed when medical device 600 is in operation, and the end of the tube features a relatively soft distal tip 616. Therefore, central tube 602 is unlikely to make inadvertent contact with the vessel walls and cause unintended tissue damage. However, central tube 602 may comprise any material which is biocompatible and provides sufficient structure, including materials discussed in regards to other exemplary embodiments.

Figure 7:
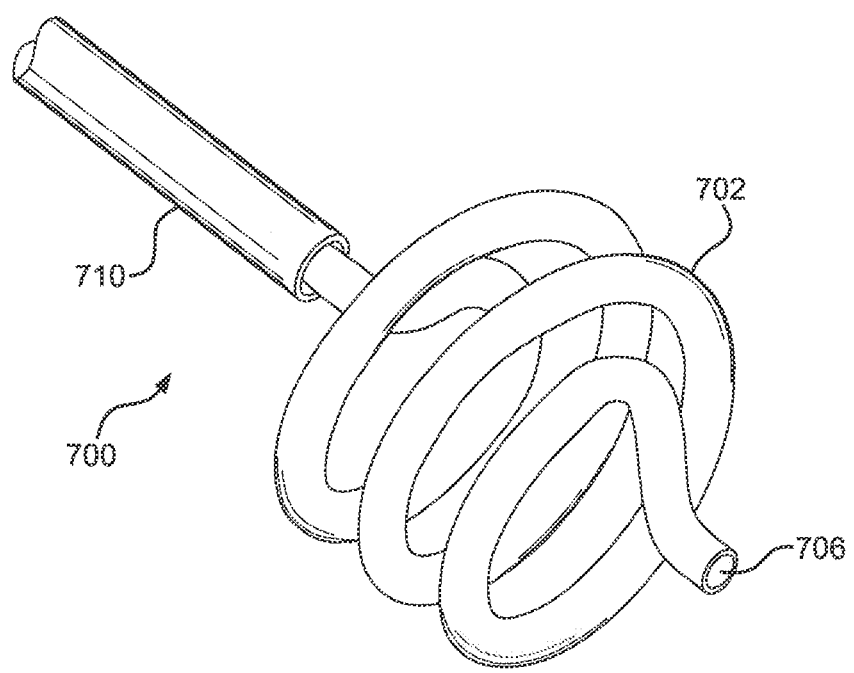
FIG. 7 illustrates a side view of another exemplary medical device, comprising a "pigtail" type anchoring device.

With reference to FIG. 7, medical device 700 may comprise a central tube 702 which contains a single lumen 706 and extends beyond the distal end of an outer tube 710. In various exemplary embodiments, the portion of central tube 702 which extends beyond the distal end of outer tube 710 may change shape and configuration. For example, the exposed portion of central tube 702 may be configured in a "pigtail" configuration. In this embodiment, the "pigtail" is made by forming the distal end of central tube 702 into a spiral at the distal region large enough in diameter to contact adjacent tissues. In this configuration, the "pigtail" shape of the exposed portion of central tube 702 positions and centers medical device 700 in the treatment vessel by contacting the side walls of the vessel. This positioning helps to reduce inadvertent contact between medical device 700 and the walls of the treatment vessel, minimizing damage to the tissue and reducing the risk of vascular stenosis.

Figure 8:
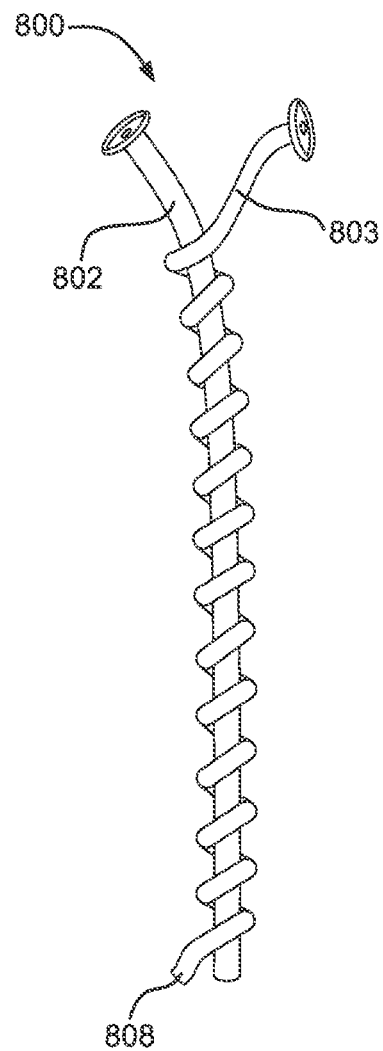
FIG. 8 illustrates a side view of an exemplary medical device comprising a secondary tube.

In various exemplary embodiments, medical devices in accordance with the present disclosure may further comprise a secondary tube. As illustrated in FIG. 8, secondary tube 803 may be configured to spiral along the outside of central tube 802. In this configuration, secondary tube 803 houses second lumen 808.

Secondary tube 803 may comprise, for example, a biocompatible material. Such materials may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be used.

In an aspect of the exemplary embodiments, secondary tube 803 may provide structural support to medical device 800. Central tube 802 and secondary tube 803 may comprise a flexible material, such as ePTFE, which allows central tube 802 and secondary tube 803 to be in a collapsed configuration when medical device 800 is not in use. When medical device 800 is in operation, blood returning to the vessel from treatment inflates secondary tube 803, providing structural support to central tube 802. When medical device 800 is not in operation, central tube 802 will float in the flow of blood within the treatment vessel. This configuration reduces the force and/or impact with which medical device 800 contacts the walls of the treatment vessel, decreasing tissue damage and reducing the risk of vascular stenosis.

Figure 9:
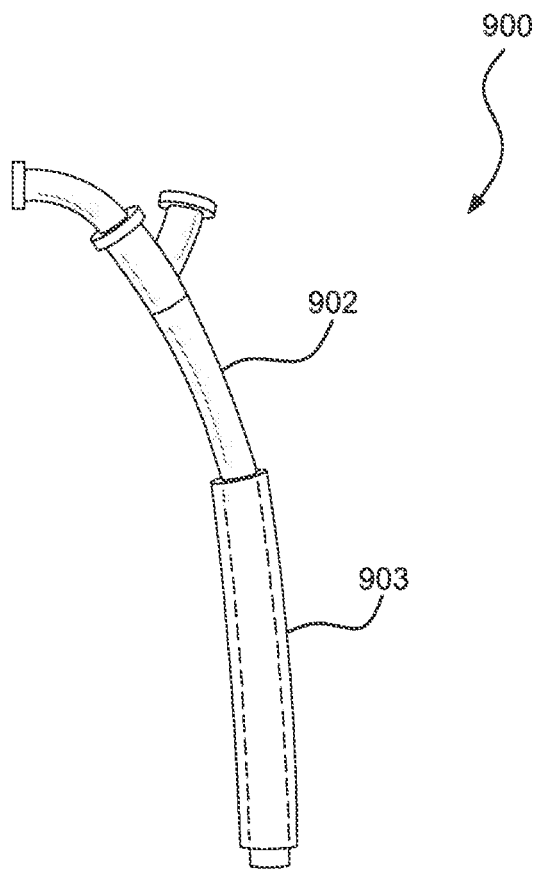
FIG. 9 illustrates a side view of another exemplary medical device comprising a secondary tube.

With reference to FIG. 9, an exemplary medical device 900 comprises a secondary tube 903 which surrounds central tube 902. In various exemplary embodiments, central tube 902 and secondary tube 903 may comprise multiple configurations. For example, central tube 902 and secondary tube 903 may comprise an expanded configuration when medical device 900 is in operation and a collapsed configuration when medical device 900 is not in operation. As used herein, "expanded" means being swelled, unfurled or otherwise having an increased diameter and/or an increased volume. "Collapsed" means being compressed, closed, furled or otherwise having a decreased diameter and/or a decreased volume.

For example, secondary tube 903 may comprise an inflatable sleeve which extends from the distal end of medical device 900 to the proximal end of central tube 902. When medical device 900 is in operation, secondary tube 903 inflates to an expanded configuration and provides structural support to central tube 902. In an aspect of these exemplary embodiments, secondary tube 903 inflates to a diameter that makes contact with the inner vessel walls. When medical device 900 is not in operation, secondary tube 903 deflates to a collapsed configuration in which the tube does not contact the inner vessel walls. The expansion and collapse of secondary tube 903 may reduce the formation of biofilm and/or biofouling on the outside surface of the tube.

In various exemplary embodiments, secondary tube 903 may comprise a perforated material, such as ePTFE. In this configuration, treated blood is returned to the treatment vessel through the walls of secondary tube 903. In an aspect of various exemplary embodiments, therapeutic agent may also pass through the secondary tube 903 and into the treatment vessel. Secondary tube 903 may also be rendered elastomeric by the incorporation of an elastomeric compound such as is taught in U.S. Patent Application Publication 2004/0024448 to Chang et al., which is incorporated by reference herein in its entirety.

Figure 10A:
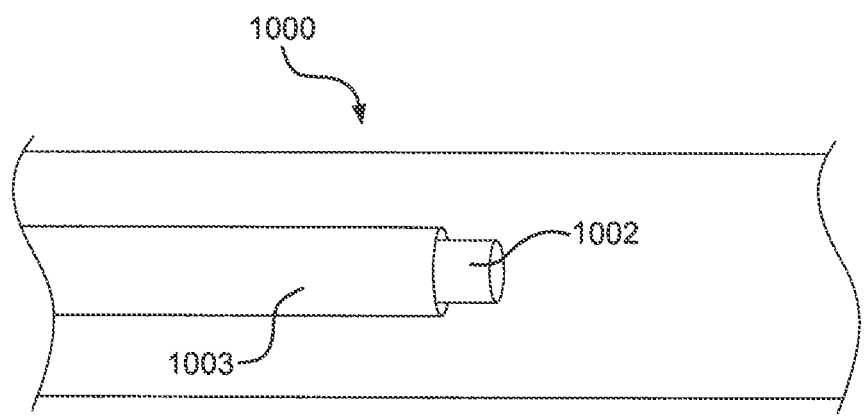
FIGS. 10A and 10B illustrate a side view of an exemplary medical device comprising a secondary tube.
Figure 10B:
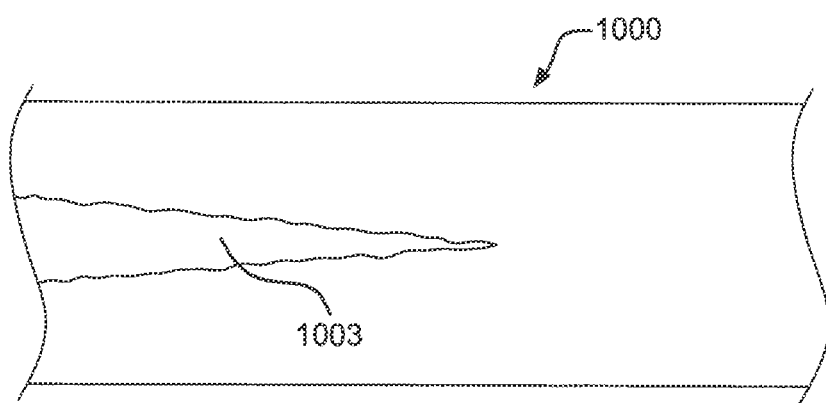

With reference to FIGS. 10A and 10B, an exemplary medical device 1000 comprises a central tube 1002 and a secondary tube 1003. In various exemplary embodiments, secondary tube 1003 is a sleeve which may be implanted in a patient's vasculature. As illustrated in FIG. 10A, central tube 1002 may be inserted into secondary tube 1003 to provide treatment to a patient's vasculature, and removed once treatment has been completed.

In various exemplary embodiments, secondary tube 1003 may comprise an expanded configuration when medical device 1000 is in operation and a collapsed configuration when medical device 1000 is not in operation. For example, secondary tube 1003 may comprise a collapsible sleeve which extends from the distal end of medical device 1000 to the proximal end of central tube 1002. When medical device 1000 is in operation, central tube 1002 is inserted into secondary tube 1003, opening secondary tube 1003 to an expanded configuration. When medical device 1000 is not in operation, central tube 1002 is removed from secondary tube 1003, allowing secondary tube 1003 to collapse.

Secondary tube 1003 may comprise, for example, a highly flexible biocompatible polymeric material such as ePTFE. As illustrated in FIG. 10B, secondary tube 1003 is flexible enough that, in the absence of central tube 1002, it collapses within the treatment vessel and seals itself. This prevents blood from flowing back into secondary tube 1003 when treatment is not being provided to the patient.

In other exemplary embodiments, secondary tube 1003 may further comprise an anchoring segment. In an aspect of these exemplary embodiments, the anchor segment may be configured as a "Chinese lantern" shape. In this configuration, the legs of the anchor segment may be deployed from a collapsed configuration, in which they are substantially parallel to central tube 1002, to an expanded configuration, in which they contact the vessel walls in a "Chinese lantern" shape. The legs of the anchor segment may contact the walls of the treatment vessel, stabilizing and centering medical device 1000 while treatment is delivered to the patient. Any shape or configuration of the anchor segment which centers and stabilizes medical device 1000 within the treatment vessel is within the scope of the invention.

Figure 11A:
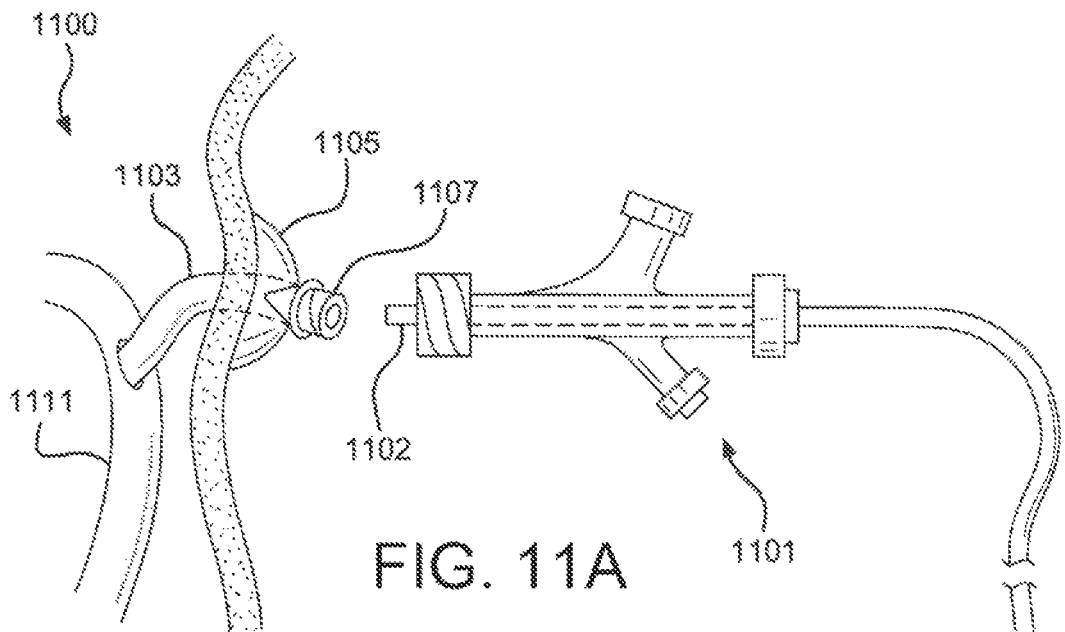
FIGS. 11A and 11B illustrate an exemplary medical device comprising a port.
Figure 11B:
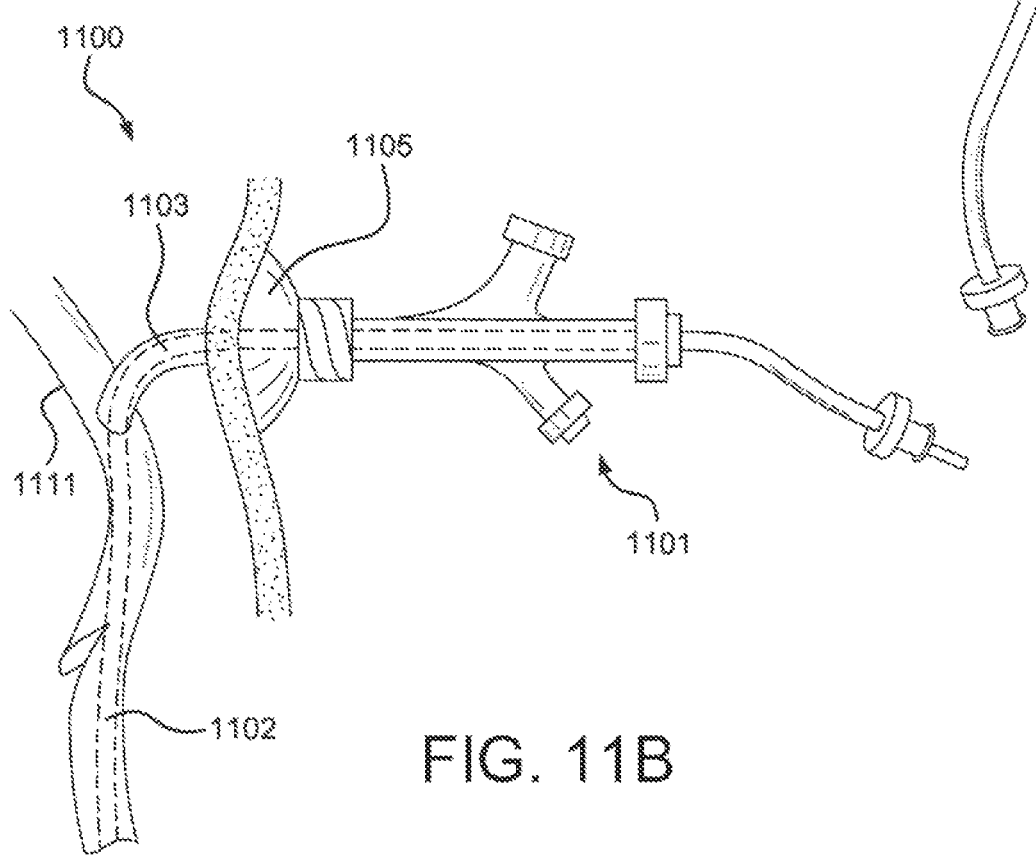

With reference to FIG. 11, an exemplary medical device 1100 comprises a catheter body 1101, which houses a central tube 1102. Medical device 1100 further comprises a port 1105 with a port opening 1107 and a secondary tube 1103. Port 1105 is installed in the patient's skin, and secondary tube 1103 is installed between the subdural portion of port 1105 and a treatment vessel 1111. In this configuration, port opening 1105 is in fluid communication with treatment vessel 1111 through secondary tube 1103.

Catheter body 1101 may be attached to port 1105 and port opening 1107. Central tube 1102 may then be inserted through port opening 1107 into secondary tube 1103. Central tube 1102 is advanced through secondary tube 1103 into treatment vessel 1111. Once central tube 1102 is in position within treatment vessel 1111, treatment may begin. When treatment has completed, central tube 1102 may be removed from treatment vessel 1111 and secondary tube 1103 for cleaning or disposal. Port opening 1107 may then be sealed to prevent fluid leakage from the patient's vasculature.

Figure 12A:
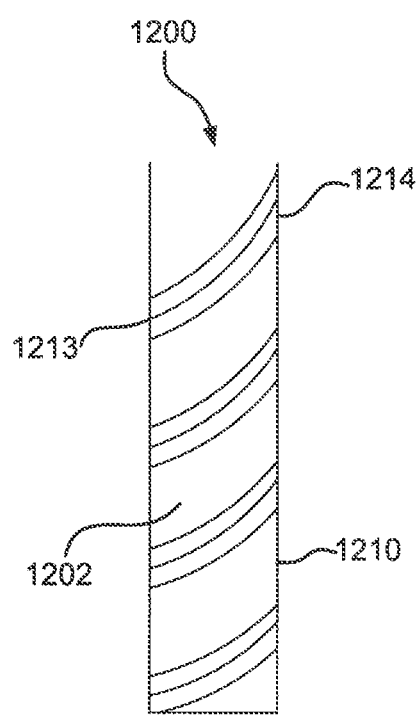
FIGS. 12A and 12B illustrate an exemplary medical device comprising a support wire path and support wire.
Figure 12B:
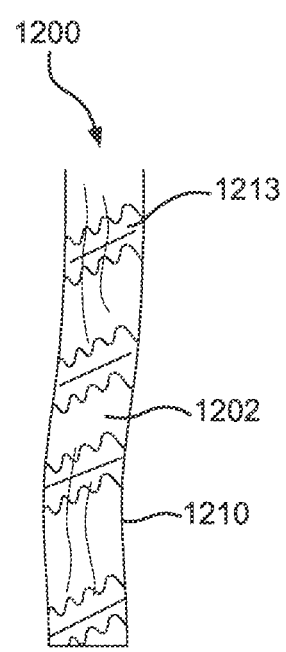

With reference to FIG. 12, an exemplary medical device 1200 comprises a central tube 1202, jacket 1210, support wire path 1213, and a support wire 1214. In this configuration, support wire path 1213 is integral to jacket 1210, and may comprise a spiral-shaped groove in jacket 1210. As illustrated in FIG. 12A, support wire 1214 may be inserted into support wire path 1213, providing shape and structural support to central tube 1202. Support wire 1214 may comprise a metallic material, such as a stainless steel or nitinol stylet. Any material which provides sufficient support such that support wire 1214 has adequate strength to maintain the desired shape of central tube 1202 and jacket 1210 is within the scope of the present disclosure.

Once support wire 1214 is inserted into support wire path 1213, treatment may be provided to the patient's vasculature. When treatment has concluded, support wire 1214 may be removed from support wire path 1213, allowing central tube 1202 to adopt a relaxed configuration.

Central tube 1202 may comprise a relatively flexible material, such as ePTFE. The relatively flexible material allows central tube 1202 to float in the flow of blood within the treatment vessel, minimizing inadvertent contact with the vessel walls and decreasing potential tissue damage. Central tube 1202 may comprise any biocompatible material which allows central tube 1202 to assume a relaxed configuration after support wire 1214 is removed.

Figure 13:
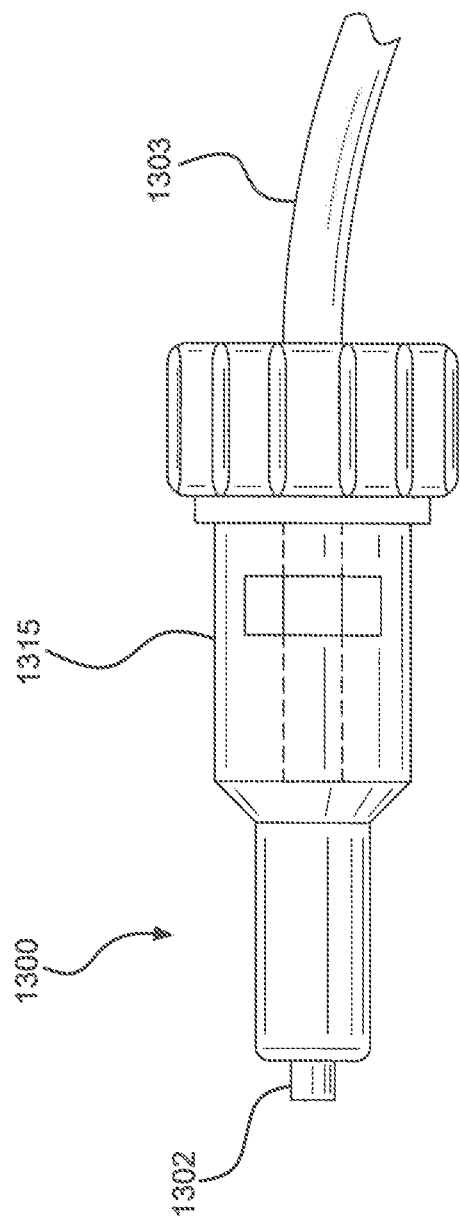
FIG. 13 illustrates an exemplary medical device comprising a docking station.

With reference to FIG. 13, an exemplary medical device 1300 comprises a catheter tube 1302 and docking station 1315. In this configuration, catheter tube 1302 is positioned inside of docking station 1315. Treated blood is pumped in to docking station 1315. The pressure of the returning blood flow causes catheter tube 1302 to telescope out of docking station 1315, through a port, and into the treatment vessel for the duration of treatment. Once treatment has completed, catheter tube 1302 may be retracted into docking station 1315. In another embodiment, central tube 1303 may be passed through docking station 1315 and inserted into catheter tube 1302 to unfurl, expand, extend and/or provide support for catheter tube 1302 during a treatment. In another embodiment, after treatment, central tube 1303 is removed from catheter tube 1302 allowing retraction and/or retracting catheter tube 1302 into docking station 1315. Between treatments, a substantial portion and/or distal end of catheter tube 1302 may remain within docking station 1315.

In various exemplary embodiments, such as those illustrated in FIG. 1, the proximal portion of central tube 102 may comprise a plurality of single-lumen extension tubes 106, 108 and 110. In addition, each extension tube can comprise a connector hub 112, 114 and 116. Connector hubs 112, 114 and 116 may be configured for selective sealable attachment between the proximal end of the proximal extension tubes and legs of a fluid exchange device, or other device, such as a syringe. In one embodiment, connector hubs 112, 114 and 116 are connectable with mating compression fittings. In another embodiment, connector hubs 112, 114 and 116 comprise luer-type fittings. Any attachment means which permits connector hubs 112, 114 and 116 to maintain proper fluid communication with a fluid exchange device is within the scope of the present disclosure.

In various exemplary embodiments, such as those illustrated in the various figures, the central tube, jacket, and various lumens may be disposable. Such disposable embodiments may be discarded after a single treatment is completed. In other embodiments, various components of the medical devices may be sterilized for re-use. For example, in various exemplary embodiments, medical devices may be exposed to ultrasonic energy as a component of the sterilization cycle. However, any technique which sufficiently sterilizes and prepares exemplary medical devices for re-use is within the scope of the present disclosure.

In various exemplary embodiments, medical devices of the present disclosure may be cleaned and/or sterilized while they are positioned in a patient's vasculature. For example, ultrasonic energy may be applied to an exemplary medical device which is positioned in a patient. The resultant vibration may reduce or remove biofouling, such as biofilm, that has accumulated on the surface of the portion of medical device in the patient's body.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

The invention claimed is:

1. A medical device comprising:
a central tube including a first lumen and a second lumen, wherein an outer surface of the central tube comprises a plurality of grooves extending along the longitudinal axis of the central tube, wherein the first lumen and the second lumen each have circular cross section;
an outer jacket surrounding the central tube, wherein the grooves and the jacket form a plurality of channels extending along at least a portion of the longitudinal axis of the central tube; and
a distal tip attached to a distal end of the central tube, wherein the distal tip is wedge-shaped or flapper-shaped.

2. The medical device of claim 1, wherein the central tube defines a substantially oval-shaped outer profile.

3. The medical device of claim 1, the central tube being configured to fluidly couple with a port opening of a port which is installed in a patient's skin.

4. The medical device of claim 1, the outer jacket further comprising a support wire pathway and a support wire inserted into the support wire pathway.

5. The medical device of claim 1, wherein the outer jacket is formed of ePTFE having a permeable microstructure.

6. The medical device of claim 1, wherein the outer jacket is permeable to a therapeutic agent delivered through one or more of the plurality of channels.

7. The medical device of claim 1, wherein a distal end of the outer jacket includes a plurality of sections configured to bend and expand radially into a larger diameter anchor section.

8. The medical device of claim 1, wherein the first lumen is in fluid communication with a first extension tube and the second lumen is in fluid communication with a second extension tube.

9. The medical device of claim 1, further comprising a plurality of extension tubes each attached to a different channel of the plurality of channels.

10. The medical device of claim 1, wherein the outer jacket further forms a support wire path integral to the outer jacket that is configured to receive a support wire therein to provide shape and structural support to the central tube.

11. A medical device comprising:
a central tube including a first lumen and a second lumen, wherein an outer surface of the central tube comprises a plurality of grooves extending along the longitudinal axis of the central tube, wherein the first lumen and the second lumen each have circular cross section;
an outer jacket surrounding the central tube, wherein the grooves and the jacket form a plurality of channels extending along at least a portion of the longitudinal axis of the central tube;
a docking station configured to pump treated blood; and
a secondary tube positioned inside the docking station such that a pressure of returning blood flow causes the secondary tube to telescope out of the docking station and into a treatment vessel.

12. A medical device comprising:
a central tube comprising at least one lumen;
an outer tube concentrically surrounding the central tube, wherein the outer surface of the outer tube comprises a plurality of grooves extending along the longitudinal axis of the outer tube; and an outer jacket surrounding the outer tube, wherein the grooves and the jacket form a plurality of channels extending along at least a portion of the longitudinal axis of the outer tube, wherein the distal end of the central tube is longer than the distal end of the outer tube, and the portion of the central tube which extends past the outer tube comprises a pigtail-shaped vessel anchor.

13. The medical device of claim 12, the central tube being configured to fluidly couple with a port opening of a port which is installed in a patient's skin.

14. The medical device of claim 12, the outer jacket further comprising a support wire pathway and a support wire inserted into the support wire pathway.

15. The medical device of claim 12, further comprising:
a docking station configured to pump treated blood; and
a secondary tube positioned inside the docking station such that a pressure of returning blood flow causes the secondary tube to telescope out of the docking station and into a treatment vessel.

16. A medical device comprising:
a central tube comprising at least one lumen, wherein an outer surface of the central tube comprises a plurality of grooves extending along the longitudinal axis of the central tube;
an outer jacket surrounding the central tube, wherein the grooves and the jacket form a plurality of channels extending along at least a portion of the longitudinal axis of the central tube; and
a secondary tube which spirals around the central tube and the jacket.

17. The medical device of claim 16, the central tube being configured to fluidly couple with a port opening of a port which is installed in a patient's skin.

18. The medical device of claim 16, the outer jacket further comprising a support wire pathway and a support wire inserted into the support wire pathway.

19. The medical device of claim 16, further comprising:
a docking station configured to pump treated blood; and
a secondary tube positioned inside the docking station such that a pressure of returning blood flow causes the secondary tube to telescope out of the docking station and into a treatment vessel.

20. A medical device comprising:
a central tube including a first lumen and a second lumen, wherein an outer surface of the central tube comprises a plurality of grooves extending along the longitudinal axis of the central tube, wherein the first lumen and the second lumen each have circular cross section; and
an outer jacket surrounding the central tube, wherein the grooves and the jacket form a plurality of channels extending along at least a portion of the longitudinal axis of the central tube, and the outer jacket defines a support wire path that is integrally formed within the outer jacket for receiving a support wire therein to provide shape and structural support to the central tube.

* * * * *